US008506905B2

(12) United States Patent
Takeuchi et al.

(10) Patent No.: US 8,506,905 B2
(45) Date of Patent: Aug. 13, 2013

(54) METHOD OF FORMING BILAYER MEMBRANE BY CONTACT BETWEEN AMPHIPATHIC MONOLAYERS AND APPARATUS THEREFOR

(75) Inventors: Shoji Takeuchi, Bunkyo-ku (JP); Hiroaki Suzuki, Bunkyo-ku (JP); Kei Funakoshi, Bunkyo-ku (JP)

(73) Assignee: The University of Tokyo, Tokyo (JP)

( * ) Notice: Subject to any disclaimer, the term of this patent is extended or adjusted under 35 U.S.C. 154(b) by 793 days.

(21) Appl. No.: 11/997,058

(22) PCT Filed: Jul. 26, 2006

(86) PCT No.: PCT/JP2006/314741
§ 371 (c)(1),
(2), (4) Date: Mar. 3, 2008

(87) PCT Pub. No.: WO2007/013493
PCT Pub. Date: Feb. 1, 2007

(65) Prior Publication Data
US 2010/0147450 A1  Jun. 17, 2010

(30) Foreign Application Priority Data

Jul. 29, 2005  (JP) ................................. 2005-220002

(51) Int. Cl.
*B01L 3/00* (2006.01)
*G01N 1/16* (2006.01)
*G01N 31/20* (2006.01)
*B01D 11/00* (2006.01)
*B01D 35/00* (2006.01)

(52) U.S. Cl.
USPC ........... 422/502; 210/205; 210/258; 422/501; 422/504; 422/505; 422/551; 422/552; 435/288.4; 435/288.5; 435/287.3

(58) Field of Classification Search
USPC ......... 210/150, 199, 205, 252, 258; 156/245, 156/500; 422/99, 100, 102, 104, 501, 502, 422/504, 505, 551, 552; 435/288.4, 288.5, 435/287.3; 436/174, 180
See application file for complete search history.

(56) References Cited

U.S. PATENT DOCUMENTS

| H201 H | * | 1/1987 | Yager | 436/51 |
| 7,595,195 B2 | * | 9/2009 | Lee et al. | 436/52 |
| 2004/0225249 A1 | * | 11/2004 | Leonard et al. | 604/4.01 |
| 2006/0076295 A1 | * | 4/2006 | Leonard et al. | 210/645 |

FOREIGN PATENT DOCUMENTS

| JP | 2005 91305 | 4/2005 |
| JP | 2005 98718 | 4/2005 |

* cited by examiner

*Primary Examiner* — John Kim
(74) *Attorney, Agent, or Firm* — Oblon, Spivak, McClelland, Maier & Neustadt, L.L.P.

(57) ABSTRACT

The present invention provides simple and an accurate apparatuses for forming bilayer membranes by the contact of amphipathic monolayers. In one apparatus, amphipathic monolayers are brought into contact and fused by controlling the pressure of liquids introduced from microchannels forming an intersection containing a chamber. In another apparatus, the chamber includes a number of compartments and at least one construction portion. In this apparatus, a droplet is formed within each compartment and contact of amphipatic monolayers is accomplished by adjusting the size of the droplets.

17 Claims, 11 Drawing Sheets

FIG. 9
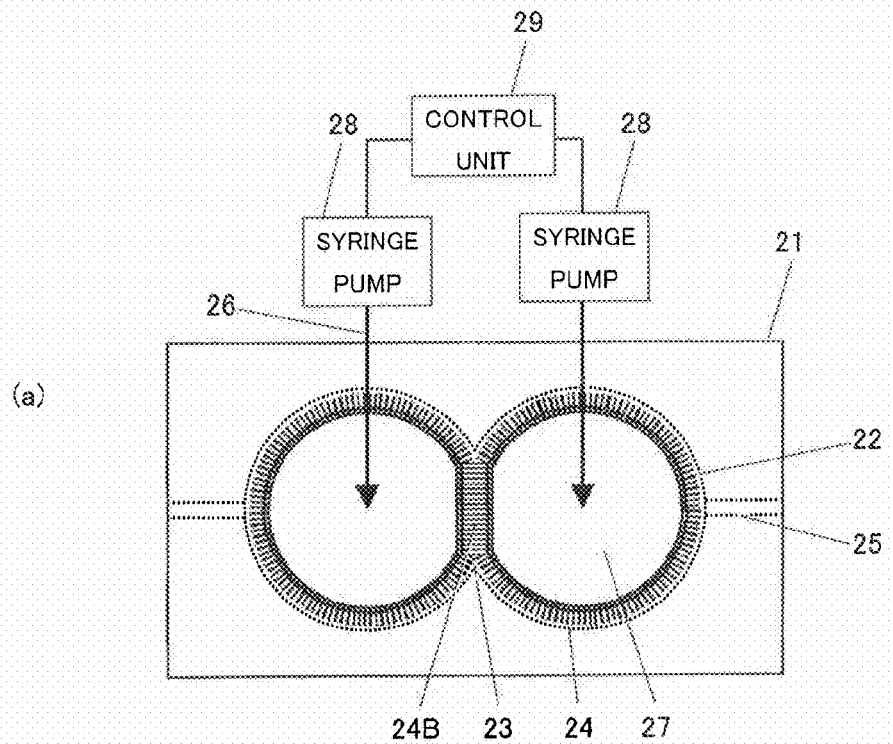
(a)
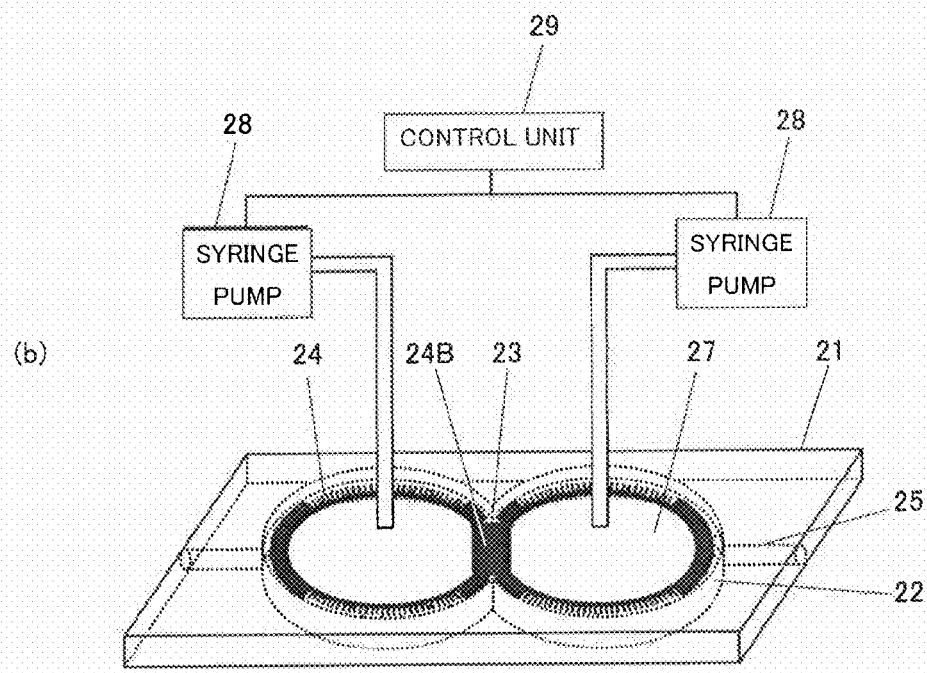
(b)

METHOD OF FORMING BILAYER MEMBRANE BY CONTACT BETWEEN AMPHIPATHIC MONOLAYERS AND APPARATUS THEREFOR

TECHNICAL FIELD

The present invention relates to a method and an apparatus of forming a bilayer membrane for analyzing membrane proteins used in the field of biotechnology, biochips, analysis of membrane proteins, drug screening assays, and biosensors.

BACKGROUND ART

Membrane proteins, which are present in cell membranes, play an important role in immune reactions and material transports/releases to inside and outside of the cells. Therefore, for the development of the method of therapy and drug discovery in the next generation, it is an important subject to clarify each functions and characteristics of various kinds of membrane proteins.

Typical conventional art for fabricating planar lipid membranes used for analyzing membrane proteins such as an ion channel is a planar membrane method, i.e., brush coating method or LB method (Langmuir-Blodgett method). In both of the methods, a lipid bilayer is formed in a tiny aperture of several hundred microns in size pierced on a Teflon (a trademark) sheet in a chamber filled with buffer solution. In the method of the former, lipid solution is coated on the tiny aperture with a brush. On the other hand, in the method of the latter, the planar lipid membrane is formed by gradually rising solution surface in the chamber on both sides of a Teflon (a trademark) sheet, using such effect that a lipid monolayer is formed on the liquid surface.

FIG. 1 is a schematic view of a conventional LB method of forming a planar lipid bilayer membrane.

In this figure, 101 is a Teflon (a trademark) sheet, 102 is a tiny aperture pierced on the Teflon (a trademark) sheet 101, 103 is the solution on the surface of which a lipid monolayer 104 is formed, and 105 is a buffer solution, and a lipid bilayer membrane 106 is formed by gradually rising the surface of the solution 103 in the chamber on both sides of the Teflon (trademark) sheet 101.

The following are examples of the other methods which have been proposed to the present for forming a lipid bilayer membrane:
(1) A method of forming a lipid bilayer membrane by extending amphipathic molecules at the interface of a liquid trilayer system and removing an intermediate liquid layer (See patent document 1 below).
(2) A method wherein after a surface of one side of a substrate having small through-holes is made in contact with the surface of a first aqueous solution, the solution containing molecules for forming a lipid bilayer membrane is added onto the first aqueous solution in the tiny aperture, and then the second aqueous solution is provided onto the other surface of the substrate (See patent document 2 below).

[Patent document 1] Japanese Patent Application Publication No. 03-118832.
[Patent document 2] Japanese Patent Application Publication No. 05-261277.
[Non-patent document 1] "Ion Channel Reconstitution", C. Miller Ed., Plenum Press (1986).
[Non-patent document 2] H. Suzuki, K. Tabata, Y. Kato-Yamada, H. Noji, and S. Takeuchi, μTAS, 2, 246 (2004).
[Non-patent document 3] H. Suzuki, et al., 3rd Int. IEEE-EMBS Special Topic Conf. on Microtechnologies in Medicine and Biology, Hawaii, May 2005.
[Non-patent document 4] T. Ide, Y. Takeuchi, and T. Yanagida, Single molecules, 3, 33 (2002).

DISCLOSURE OF THE INVENTION

However, both methods, i.e. the brush coating method and the LB method described above, have such drawbacks that a large chamber of several cm in size is required, and that the microscopic observation is impossible because of the large dead volume. The conventional method (1) mentioned above has also a drawback that the removal of the intermediate liquid layer requires a difficult process. Moreover, the conventional method (2) mentioned above requires a great deal of time to complete all processes in that it requires the evaporation of solvent and the spontaneous thinning of the membrane both of which require a long time to be completed and suffer from low reproducibility.

As described above, the conventional methods have several problems in forming simple and accurate lipid bilayer membranes.

In view of the above described problems, the present invention provides a method and an apparatus for forming a bilayer membrane by contact between the amphipathic monolayers, which enable to obtain bilayer membranes simply and accurately.

In order to achieve the above described object, the present invention provides:

[1] A method of forming a bilayer membrane by contact of amphipathic monolayers, wherein
an organic solvent containing amphipathic molecules is introduced into a chamber formed on a substrate,
a liquid immiscible with the organic solvent are introduced into the organic solvent in plural portions,
a plurality of amphipathic monolayers are formed at the interfaces between the liquid introduced in plural portions and the organic solvent, and
the plurality of amphipathic monolayers are brought into contact with each other to form a bilayer membrane by controlling the liquid or the organic solvent in the chamber.

[2] A method of forming a bilayer membrane by contact of amphipathic monolayers according to [1], wherein
the organic solvent is introduced into a first microchannel formed on the substrate,
the liquid immiscible with the organic solvent is introduced into a second microchannel, which crosses the first microchannel from both sides of the first microchannel to form an intersection, from both ends of the second microchannel toward the intersection,
the amphipathic monolayers opposing each other are formed at the interfaces between the liquid and the organic solvent, and
the opposing amphipathic monolayers are brought into contact and fused with each other to form bilayer membrane by controlling the pressure of the liquid in the second microchannel with syringe pumps and bringing the interfaces of the liquid introduced from the both ends of the second microchannel into contact with each other.

[3] An apparatus for forming a bilayer membrane by contact of amphipathic monolayers, including:
a chamber formed on a substrate,
an organic solvent containing amphipathic molecules introduced into the chamber,
a liquid immiscible with the organic solvent and introduced into the organic solvent in plural portions, and a means for controlling to form a plurality of amphipathic monolayers at the interfaces between the liquid and the organic solvent, and to control the liquid or the organic solvent in the chamber, in which a bilayer membrane is formed by contacting the plurality of amphipathic monolayers with each other using the means for controlling.

[4] An apparatus for forming a bilayer membrane by contact of amphipathic monolayers described in [3], including:

a first microchannel formed on the substrate and the organic solvent is introduced thereto, a second microchannel crossing the first microchannel from both sides of the first microchannel to form an intersection and the liquid immiscible with the organic solvent is introduced from the both ends of the second microchannel toward the intersection, and syringe pumps controlling the pressure of the liquid in the second microchannel, in which amphipathic monolayers opposing each other are formed at the interfaces between the liquid in the second microchannel and the organic solvent, and the opposing amphipathic monolayers are brought into contact and fused with each other to form a bilayer membrane by controlling the pressure of the liquid with the syringe pumps and bringing the interfaces of the liquid introduced from the both ends of the second microchannel into contact with each other.

[5] A method of forming a bilayer membrane by contact of amphipathic monolayers as described in [1], wherein a chamber, which is separated into a plurality of compartments by a constriction portion formed on the substrate body, is filled with the organic solvent, the liquid immiscible with the organic solvent is dropped into each compartment with a pipette to arrange a plurality of liquid droplets, the amphipathic monolayers are formed at the interfaces between the plurality of liquid droplets and the organic solvent, and the interfaces of the plurality of liquid droplets are brought into contact with each other by controlling the liquid or the organic solvent, so that the amphipathic monolayers contact with each other and fuse to form a bilayer membrane.

[6] An apparatus for forming a bilayer membrane by contact of amphipathic monolayers as described in [3], including:

a chamber separated into a plurality of compartments by a constriction portion formed on the substrate body, the organic solvent introduced into the chamber, and a pipette for providing dropwise the liquid immiscible with the organic solvent into each compartment to arrange a plurality of liquid droplets, in which the amphipathic monolayers are formed at the interfaces between the liquid droplets and the organic solvent, and the interfaces of the plurality of liquid droplets brought into contact with each other by controlling the liquid or the organic solvent, so that the amphipathic monolayers contact with each other and fuse to obtain a bilayer membrane.

[7] A method of forming a bilayer membrane by contact of amphipathic monolayers as described in [1], wherein the chamber, which is separated into a plurality of compartments by a constriction portion formed on the substrate body, is filled with the organic solvent, the liquid immiscible with the organic solvent is introduced into each compartment by syringe pumps to arrange a plurality of liquid droplets, the amphipathic monolayers are formed at the interfaces between the plurality of liquid droplets and the organic solvent, and the interfaces of the plurality of liquid droplets contact with each other by controlling the liquid or the organic solvent, so that the amphipathic monolayers contact and fuse with each other to form a bilayer membrane.

[8] An apparatus for forming a bilayer membrane by contact between amphipathic monolayers as described in [3], including:

the chamber which is separated into a plurality of compartments by a constriction portion formed on the substrate, the organic solvent introduced into the chamber, and syringe pumps for introducing a liquid immiscible with the organic solvent into the each compartment to arrange a plurality of liquid droplets, in which the amphipathic monolayers are formed at the interfaces between the plurality of liquid droplets and the organic solvent, and the interfaces of the plurality of liquid droplets are brought into contact with each other by controlling the liquid with the syringe pumps, so that the amphipathic monolayers contact and fuse with each other to obtain a bilayer membrane.

[9] A method of forming a bilayer membrane by contact of amphipathic monolayers as described in [1], [2], [5], or [7], wherein the liquid is an aqueous solution.

[10] An apparatus for forming a bilayer membrane by contact of amphipathic monolayers as described in [3], [4], [6], or [8], wherein the liquid is an aqueous solution.

[11] An apparatus for forming a bilayer membrane by contact of amphipathic monolayers as described in [6] or [8], wherein the plurality of compartments is two compartments.

[12] An apparatus for forming a bilayer membrane by the contact of amphipathic monolayers as described in [6] or [8], wherein the plurality of compartments is three compartments.

[13] An apparatus for forming a bilayer membrane by the contact of amphipathic monolayers as described in [6] or [8], wherein the plurality of compartments is five compartments and the outward appearance is substantially a square shape.

BRIEF DESCRIPTION OF THE DRAWINGS

FIG. 9 is a schematic view of an apparatus for forming lipid bilayer by the contact of monolayers including a plurality of compartments having a constriction portion in accordance with the second embodiment of the present invention.

BEST MODE FOR CARRYING OUT THE INVENTION

A method of forming a bilayer membrane by the contact of amphipathic monolayers, wherein an organic solvent containing amphipathic molecules is introduced into a first microchannel formed on a substrate, a second microchannel is formed so as to cross with the first microchannel from both side of the first microchannel to form an intersection, a liquid immiscible with the organic solvent containing amphipathic molecules is introduced from both ends of the second microchannel toward the intersection, amphipathic monolayers opposing each other are formed on the interface between the liquid and the organic solvent, and the liquid introduced from the both ends of the second microchannel is brought into contact with each other by controlling the pressure of the liquid in the second microchannel with syringe pumps, so that the amphipathic monolayers opposing each other are brought into contact and fused with each other to form a bilayer membrane.

DESCRIPTION OF THE PREFERRED EMBODIMENTS

The preferred embodiments of the present invention are described below in detail.

Figure 1:
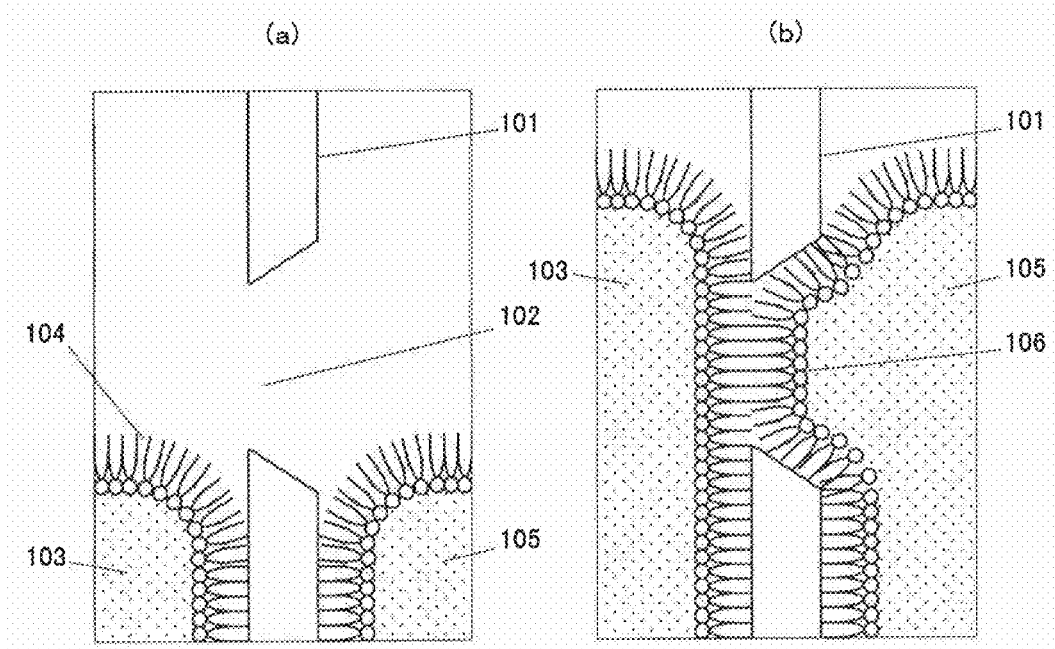
FIG. 1 is a schematic view of a method for forming a planar lipid bilayer with conventional LB method.
Figure 2:
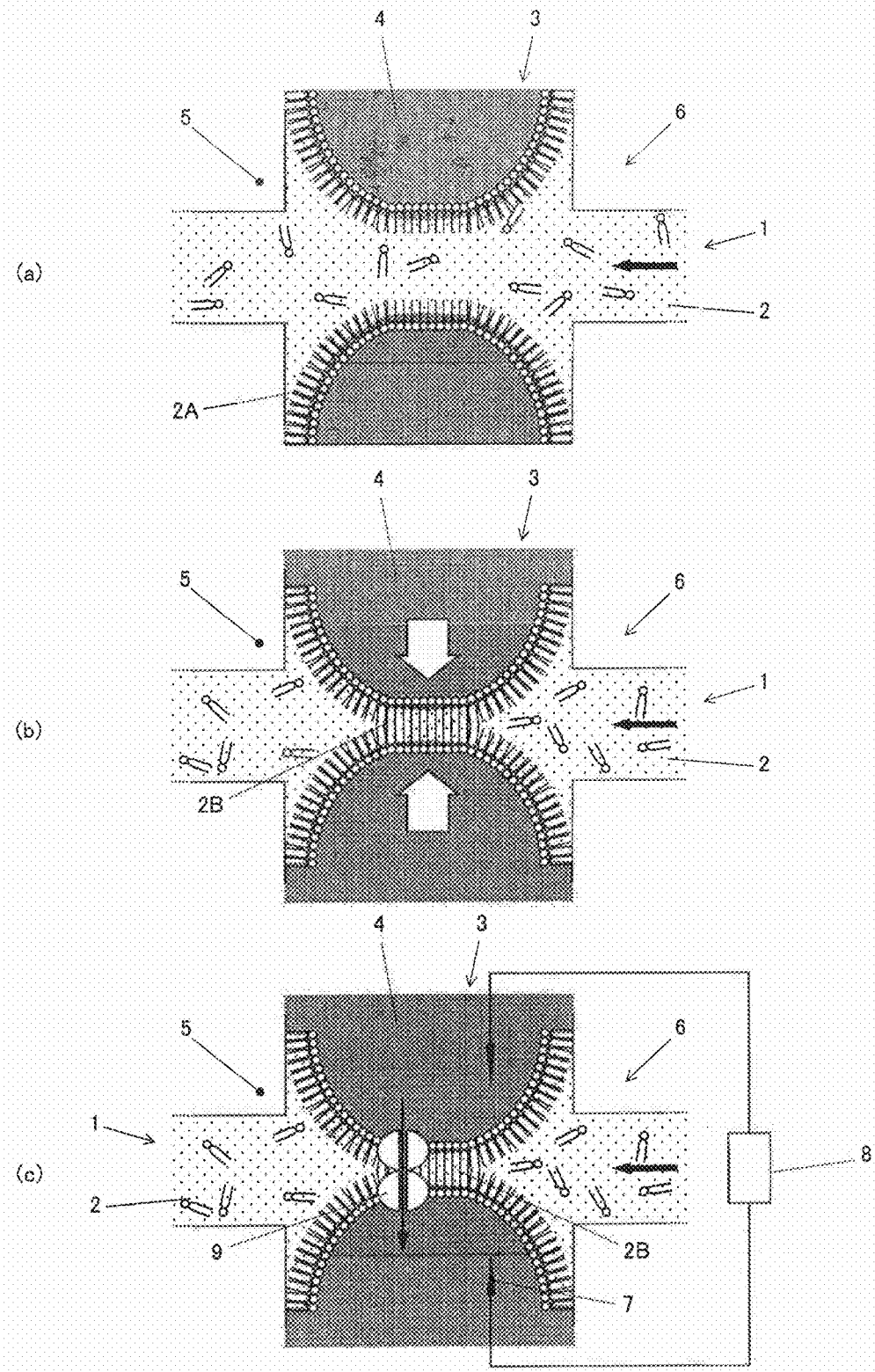
FIG. 2 is a schematic view of a method of forming a lipid bilayer by contact of monolayers using a substantially cross-shaped chamber in accordance with a first embodiment of the present invention.

FIG. 2 is a view of a method of forming a bilayer by contact of monolayers using a substantially cross-shaped chamber in accordance with a first embodiment of the present invention, and FIG. 2(a) is a view showing the state that the interfaces of aqueous solutions are not in contact with each other, while FIG. 2(b) is a view showing the state that the interfaces of aqueous solutions are in contact with each other.

Firstly, as shown in FIG. 2(a), an organic solvent 2 containing lipid molecules is introduced into a first microchannel 1 formed on a substrate 5. A second microchannel 3 is fabricated so as to cross orthogonally with the first microchannel 1, and a liquid 4 immiscible with the organic solvent 2 containing lipid molecules (for example, an aqueous solution) is introduced from the both ends of the second microchannel 3 toward the intersection of the first and the second microchannels. Syringe pumps (not shown in the view) are placed on the both ends of the second microchannel 3, and the pressure of the liquid 4 in the second microchannel 3 may be controlled by adjusting the syringe pumps. Here, the aqueous solution of KCl is used as the liquid 4 (an aqueous solution) for the purpose of electric conduction, while a conventional aqueous solution which is immiscible with the organic solvent 2 may be used for the purpose merely to form a lipid bilayer.

Accordingly, by introducing an organic solvent 2 containing lipid molecules into the first microchannel 1, and introducing a liquid 4 into the second microchannel 3, a lipid monolayer 2A is formed at the interface between the liquid 4 and the organic solvent 2 at the intersection of the cross-shaped chamber 6 where the first microchannel 1 and the second microchannel 3 crosses.

Next, the surfaces of two aqueous solutions 4 are brought closer with the control of the pressure by the injection of the liquid 4 using syringe pumps. As shown in FIG. 2(b), when the distance between the two lipid monolayers 2A becomes less than several angstroms, lipid monolayers 2A are fused into a lipid bilayer 2B by van der Waals attractive force.

As shown in FIG. 2(c), a membrane protein 9 may be also embedded in the structure of lipid bilayer of FIG. 2(b). In FIG. 2, 7 is an Ag/AgCl electrode, and 8 is a measuring apparatus for electric current and voltage.

Figure 3:
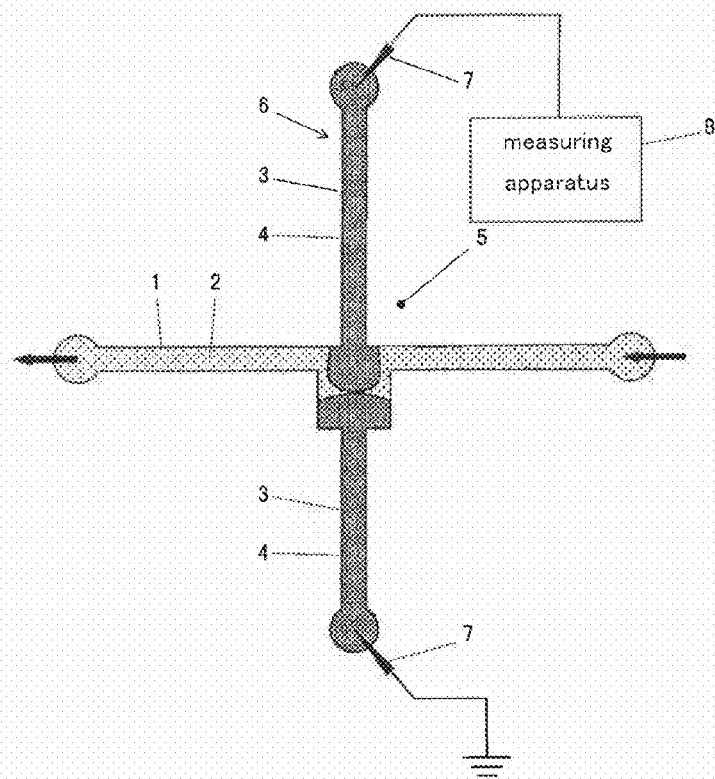
FIG. 3 is a schematic view of an apparatus of forming a lipid bilayer by contact of monolayers in accordance with the first embodiment of the present invention.

FIG. 3 is a schematic view of an apparatus for forming a lipid bilayer using the contact of monolayers in accordance with the first embodiment of the present invention.

A cross shaped chamber 6 is machined using a CAD/CAM modeling system on an acrylic resin (PMMA) substrate 5, and a thin PMMA plate is attached to the substrate 5 to close the microchannel. Both the width and the depth of the microchannel is 0.5 mm, respectively. Aqueous solution is introduced from two inlets opposing each other located in both ends of the second microchannel 3, and an organic solvent 2 containing lipid molecules is introduced from an inlet located in one end of the first microchannel 1. Here, a kind of membrane protein, Gramicidin Peptide ion channel, is used for the experiment of ionic molecular transport. In order to detect ionic flow (electric current), Ag/AgCl electrode 7 connected with a measuring apparatus 8 for electric current and voltage is inserted in two channels of the aqueous solution 4 (in this case, the KCl solution) of the second microchannel 3. As described above, the controls of the injection and the squeezing of KCl solution 4 is carried out by syringe pumps (not shown in the view), thereby an arbitrary control of the pressure or the volume of the KCl solution can be achieved.

The organic solvent 2 containing lipid molecules used in this example is a solution of 1,2-dioleoyl-sn-glycero-3-phosphocholine (DOPC, CAS No; 4235-95-4) dissolved in a chloroform-hexadecane mixture (1:1 vol %). In this experiment, 25 mg of DOPC was used. 0.5-25 mg/ml of concentration is an optimum condition. Any membrane component being possible to form a membrane, such as amphipathic molecules and surfactants can be used in place of lipids (for example, phosphatidylcholine).

Figure 4:
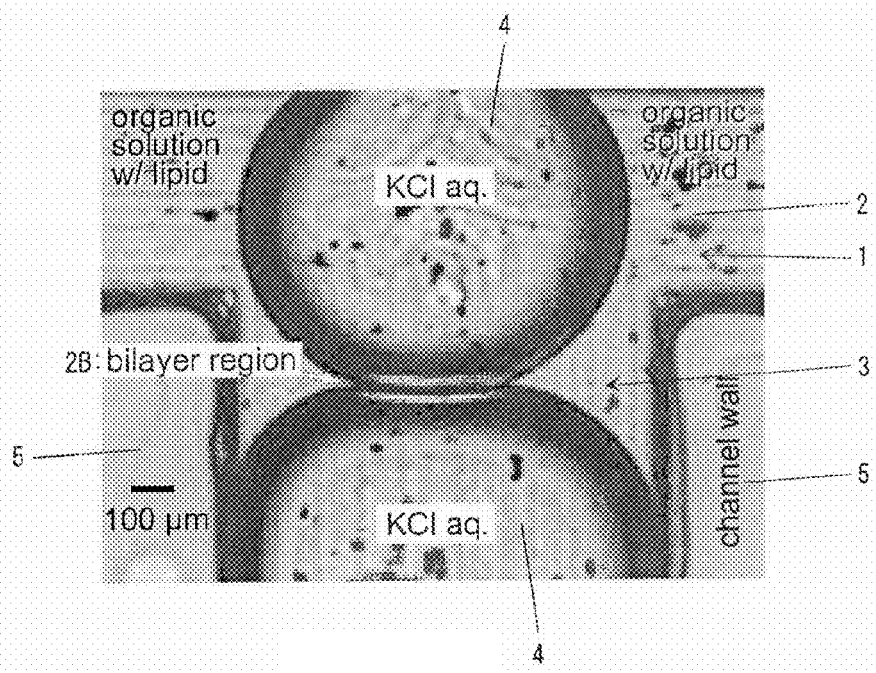
FIG. 4 is an image of an optical microscope where interfaces of aqueous solutions are in contact with each other in accordance with the first embodiment of the present invention.

FIG. 4 is an image of an optical microscope where interfaces of aqueous solutions are in contact with each other in accordance with the first embodiment of the present invention. These two aqueous solutions (KCl solutions) do not fuse because of the presence of lipid molecules on the interface. An advantage of the present invention is that the series of processes can be easily and quickly repeated again by removing the solvent in the chamber, even if the lipid bilayer is broken.

Meanwhile, the lipid bilayer operates as a capacitor because it is a thin dielectric membrane.

Figure 5:
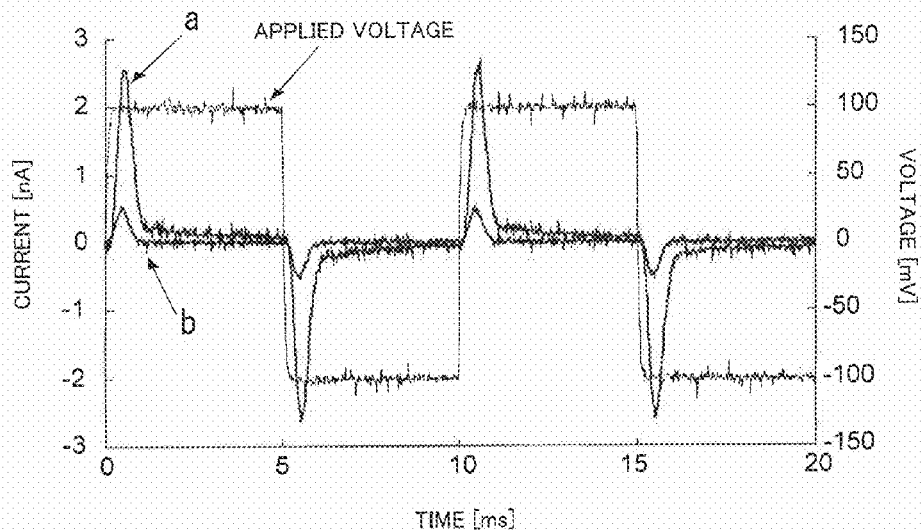
FIG. 5 is a profile of capacitive transient current passing through an interface when a 100 mV of rectangular signal is applied in accordance with the present invention.

FIG. 5 is a profile of capacitive transient current passing through interface when a 100 mV of rectangular signal is applied. A symbol "a" in the profile shows the capacitive transient current of the lipid bilayer formed by contact of lipid monolayers on the interfaces of aqueous solutions, and a symbol "b" shows the capacitive transient current in the absence of contact.

As can be seen from the FIG. 5, the characteristic behavior of membrane capacitance due to the formation of thin film emerges when a rectangular wave voltage of 100 mV (100 Hz) is applied. According to this experimental result, a membrane capacitance corresponding to as high as 130 pF was measured when the interfaces of aqueous solution come in contact with each other (symbol "a" in the view). It is thus recognized that a membrane structure of a bilayer membrane is formed on the interfaces between the two aqueous solution in contact.

Next, in order to confirm further that the lipid membrane formed above is a lipid bilayer membrane, Gramicidin Peptide ion channel which is known to open the channel synchronized with the dimer formation of each monomer component of the monolayer is introduced into the aqueous solution.

Figure 6:
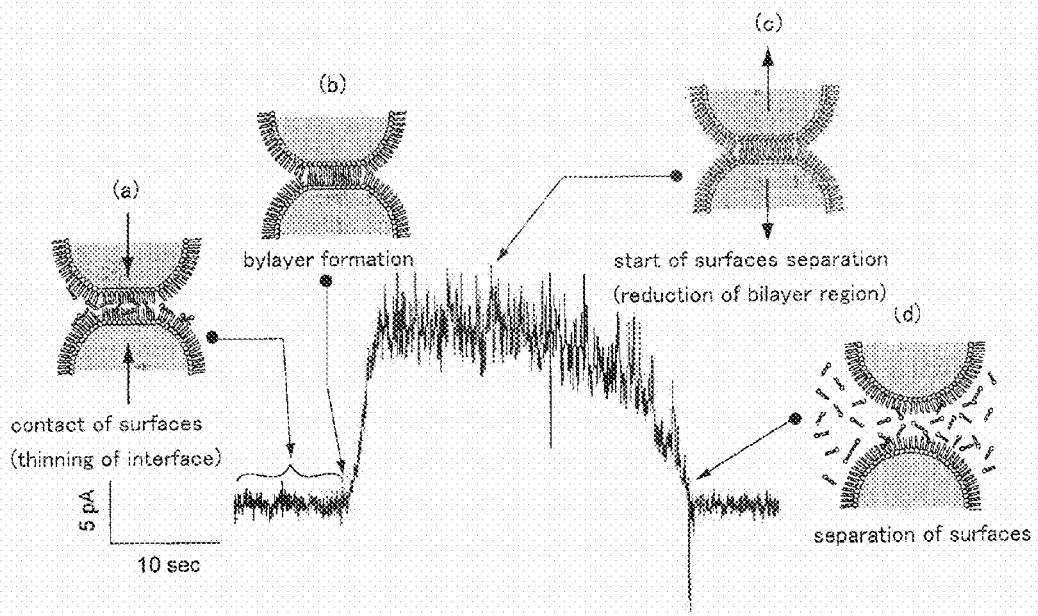
FIG. 6 is a time series of the variation of the electric current passing through a lipid bilayer embedded with Gramicidin when a 63 mV voltage is applied in accordance with an embodiment of the present invention.

FIG. 6 is a time series of the variation of the electric current passing through a lipid bilayer embedded with Gramicidin when a 63 mV voltage is applied in accordance with an embodiment of the present invention.

First, monolayers are brought into contact with each other (FIG. 6(a)). By keeping the contact of the interface of the monolayers, the electric current increases corresponding with the expansion (FIG. 6(b)) of a bilayer region. Next, the interface of the monolayers are separated by the control of syringe pumps (FIG. 6(c), (d)), then the electric current decreases to a standard value (the concentration of Gramicidin is $5.0 \times 10^{-12}$M dissolved in 100 mM of KCl).

Accordingly, the flow of $K^+$ ion (electric current) gradually increases after the contact of the interfaces of aqueous solution, which corresponds to the expansion of a bilayer region. On the other hand, the electric current decreases to zero with the separation of the interfaces. Since the Gramicidin is known to conduct electric current only when it is embedded in a bilayer, this experimental result shows the presence of a lipid bilayer during the contact of the interfaces of the aqueous solution.

As described above, lipid monolayers which are in contact with a micro fluid chip are formed in the present invention, to reconstruct the lipid bilayer in the vertical direction. The lipid bilayer of the present invention prepared from two lipid monolayers shows the same capacitance with those obtained from conventional BLM method, and a Gramicidin channel is formed in the membrane. Consequently, the membrane formed in the present invention is confirmed to be a lipid bilayer. Here, the monitoring of a membrane transport was carried out electrically with the use of this ion channel. Fluorescent imaging of the molecular transport across the membrane may be also possible using this method.

Figure 7:
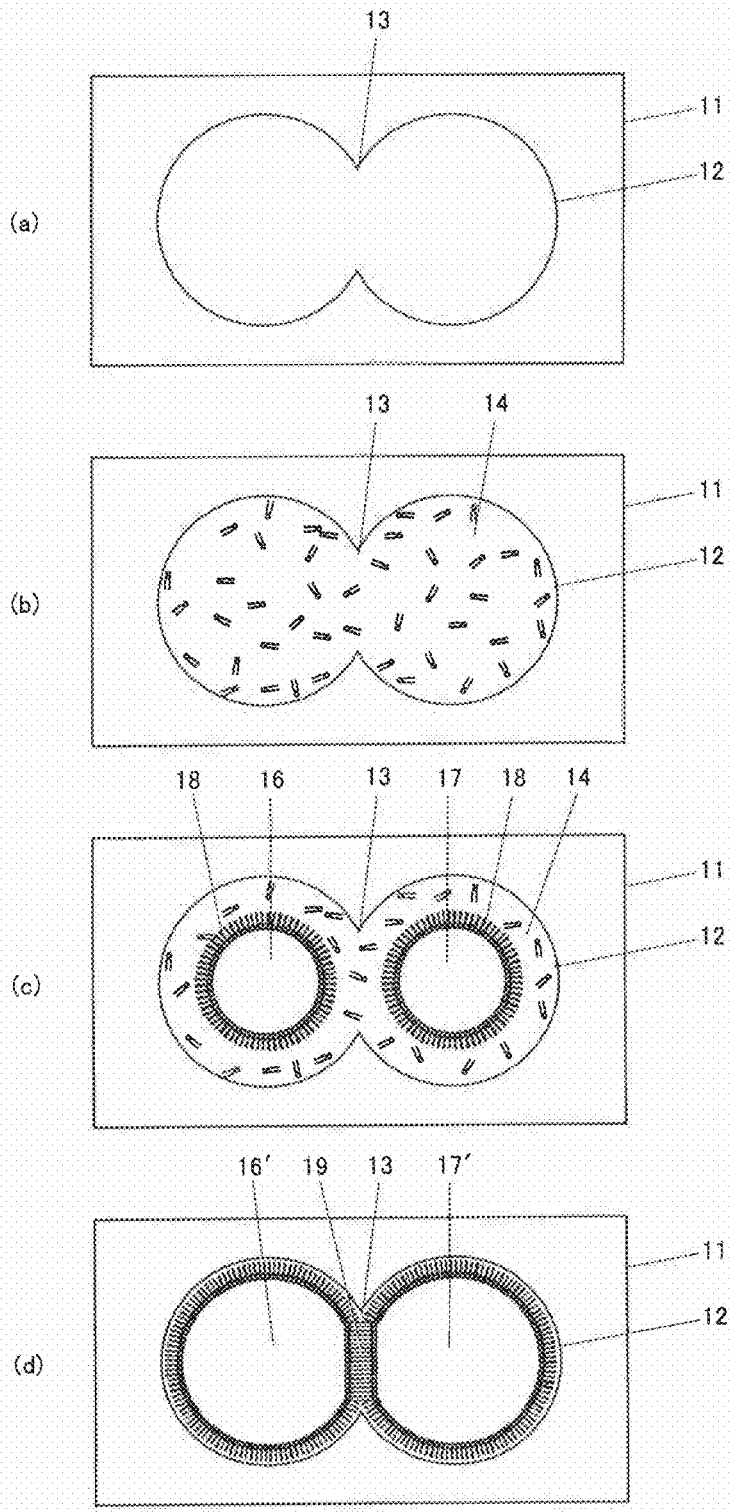
FIG. 7 is a schematic plan view of an apparatus for forming lipid bilayer by the contact of monolayers including a plurality of compartments having a constriction portion in accordance with the second embodiment of the present invention.
Figure 8:
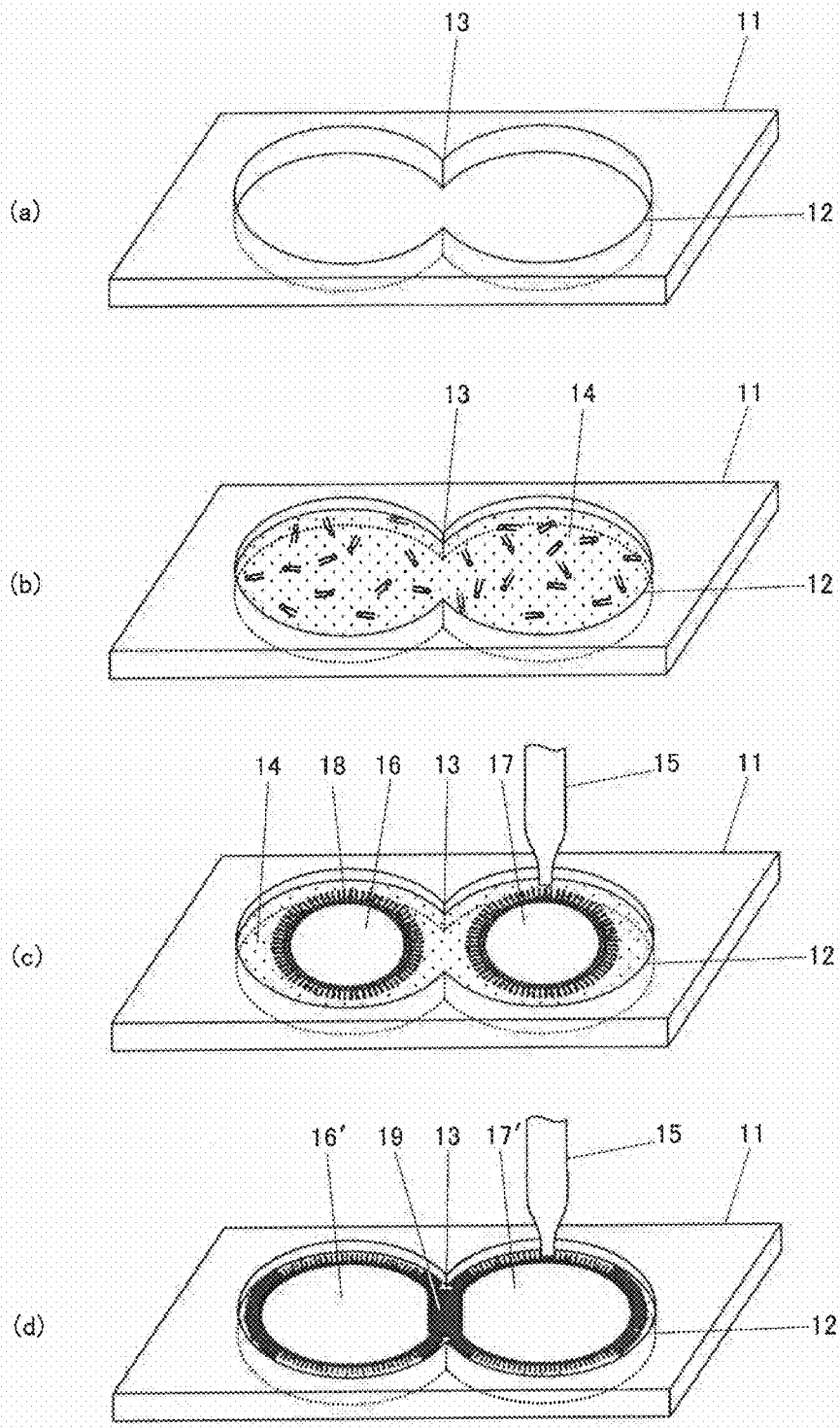
FIG. 8 is a schematic perspective view of a method of forming lipid bilayer by the contact of monolayers including a plurality of compartments having a constriction portion in accordance with the second embodiment of the present invention.

FIG. 7 is a schematic plan view of an apparatus for forming lipid bilayer by the contact of monolayers including a plurality of compartments having a constriction portion in accordance with the second embodiment of the present invention, and FIG. 8 is a schematic perspective view of a method of forming lipid bilayer using this apparatus.

Firstly, a chamber 12 separated by a constriction portion 13 is prepared on a substrate 11 opened in an upward direction as shown in FIG. 7(a) and FIG. 8(a). Next, the chamber 12 having the constriction portion 13 is filled with an organic solvent 14 containing lipid molecules as shown in FIG. 7(b) and FIG. 8(b). Next, liquid droplets 16 and 17 of an aqueous solution immiscible with the organic solvent 14 containing lipid molecules are added dropwise by a pipette 15 (see FIG. 8(c)) into each of a compartment of the chamber 12 separated by the constriction portion 13 as shown in FIG. 7(c) and FIG. 8(c). Then, in this state, lipid monolayers 18 are formed on the interface of the liquid droplets 16 and 17 of the aqueous solution and the organic solvent 14. Next, as shown in FIG. 7(d) and FIG. 8(d), the liquid droplets 16 and 17 of the aqueous solution are enlarged (the liquid droplets 16' and 17' of the aqueous solution) to bring into contact the interfaces of the liquid droplets 16' and 17' of the aqueous solution. Then the lipid monolayers 18 which are formed on the interface between the liquid droplets 16' and 17' of the aqueous solution and the organic solvent 14 containing lipid molecules are brought into contact and fused to form a lipid bilayer 19.

FIG. 9 is a schematic view of an apparatus for forming a lipid bilayer by the contact of monolayers including a plurality of compartments having a constriction portion in accordance with the second embodiment of the present invention.

In accordance with this embodiment, a chamber 22 having a constriction portion 23 which is closed with a substrate 21, includes channels 25 for feeding an organic solvent 24 containing lipid molecules, channels 26 to form liquid droplets 27 of the aqueous solution in two compartments of the chamber 22, syringe pumps 28 arranged in these channels 26, and a control unit 29 connected to these syringe pumps 28.

After the organic solvent 24 containing lipid molecules is introduced in the chamber 22 from the channels 25, the liquid droplets 27 of the aqueous solution immiscible with the organic solvent 24 containing lipid molecules are introduced from the channels 26. Then the size of the liquid droplets 27 of the aqueous solution is controlled by the syringe pumps 28, and the lipid monolayers formed on the interface between the liquid droplets 27 of the aqueous solution and the organic solvent 24 containing lipid molecules are brought into contact with each other and fused to form a lipid bilayer 24B.

Figure 10:
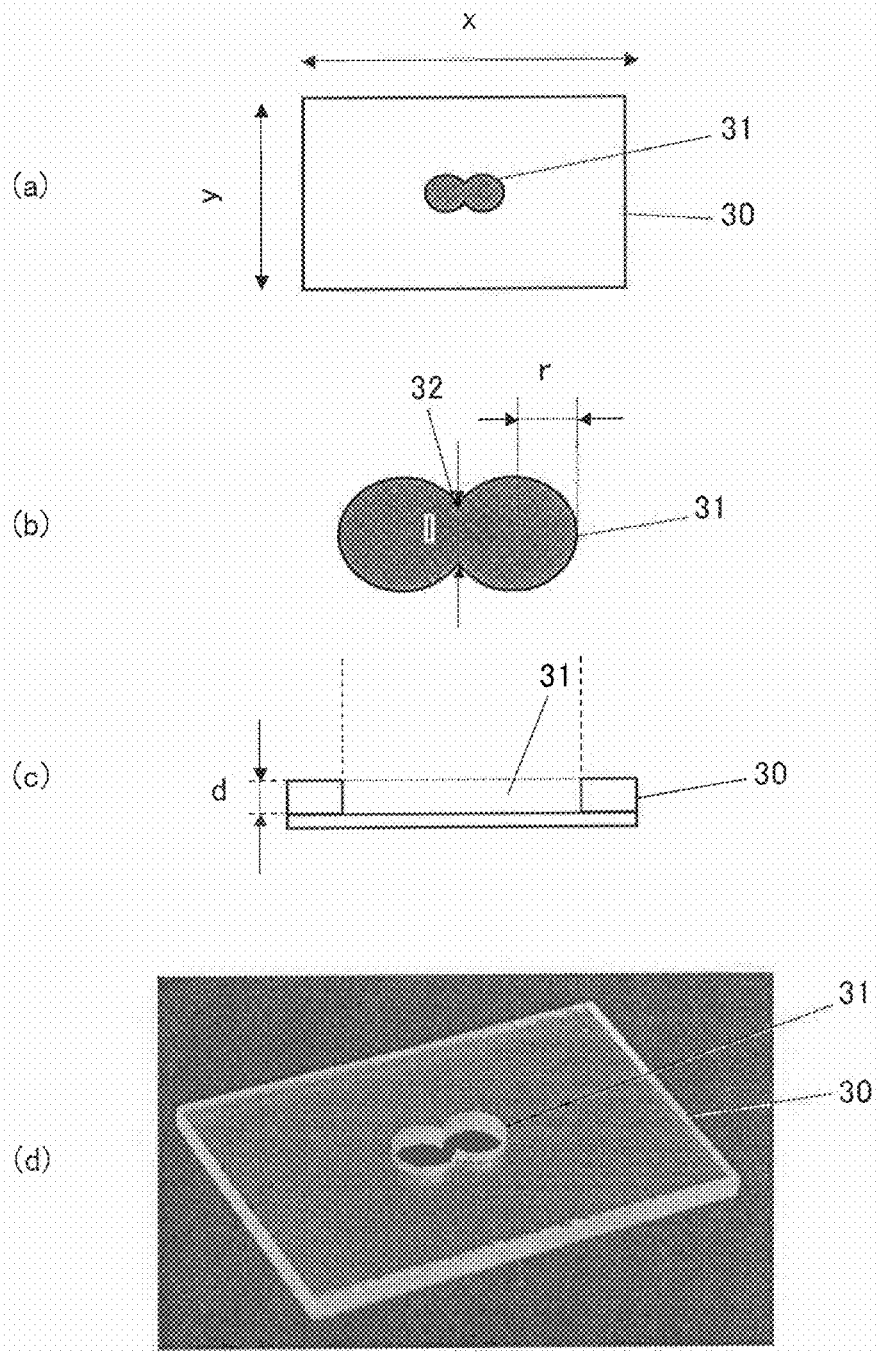
FIG. 10 is a view of the structure of a chip device including a plurality of compartments having a constriction portion in accordance with the present invention.
Figure 11:
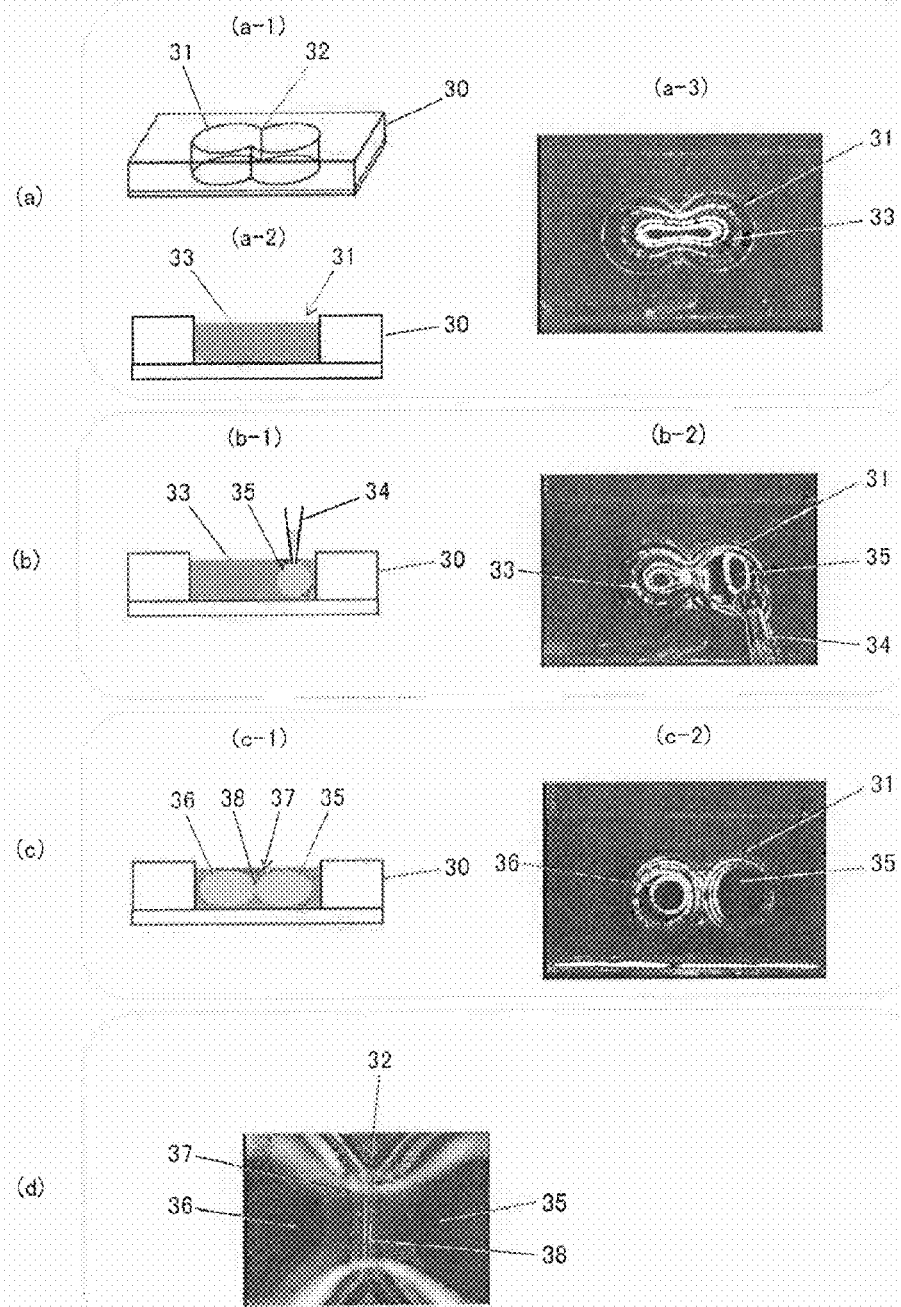
FIG. 11 is a view of a method of forming lipid bilayer in accordance with the experimental example of the present invention.

FIG. 10 and FIG. 11 show experimental examples of the present invention. FIG. 10 is a view of the structure of a chip device including a plurality of compartments having a constriction portion in accordance with the present invention. FIG. 10(a) is a top view of the whole devise, FIG. 10(b) is an enlarged plan view of chamber part, FIG. 10(c) is a side cross-sectional view of the whole device, and FIG. 10(d) is a perspective view of the whole device.

In FIG. 10(a), the length x of a substrate 30 is 30 mm and the width y is 20 mm. In FIG. 10(b), the radius r of the compartment of a chamber 31 is 2 mm and the length l between the constriction part is 2 mm. In FIG. 10(c), the thickness d of the substrate 30 is 2 mm. The material used for the substrate 30 is an acrylic resin.

FIG. 11 is a view of a method of forming lipid bilayer in accordance with the experimental example of the present invention.

(1) First, a chamber 31 as shown in FIG. 10 is filled with an organic solvent (15 µl) 33 containing lipid molecules (to be referred to FIG. 11(a-1) of a perspective view of the chip device, FIG. 11(a-2) of a side cross-sectional view of the chip device, and FIG. 11(a-3) of a top view of the chip device, respectively).

(2) Next, a first liquid drop (15 µl) 35 of aqueous solution immiscible with the organic solvent 33 is introduced into the organic solvent 33 containing lipid molecules with a pipette 34 (to be referred to FIG. 11(b-1) of a side cross-sectional view of the chip device and FIG. 11(b-2) of a top view of the chip device, respectively).

(3) Next, the second liquid drop (15 µl) 36 of aqueous solution immiscible with the organic solvent 33 containing lipid molecules is introduced ((to be referred to FIG. 11(c-1) of a side cross-sectional view of the chip device and FIG. 11(c-2) of a top view of the chip device, respectively).

(4) Then, as shown in FIG. 11(d), a lipid bilayer 38 is obtained at the constriction portion 32 at the contact part 37 between the liquid droplets 35 and 36 (to be referred to FIG. 10).

Figure 12:
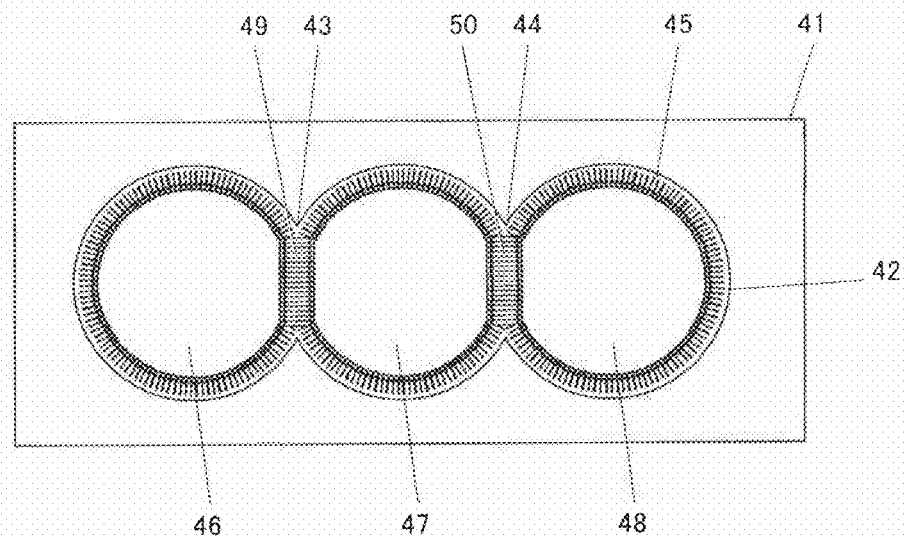
FIG. 12 is a schematic plan view of an apparatus for forming two lipid bilayers including a chamber separated into three in lateral sequences using two constriction portions in accordance with a third embodiment of the present invention.

FIG. 12 is a schematic plan view of an apparatus for forming two lipid bilayers including a chamber separated into three in lateral sequences by two constriction portions in accordance with a third embodiment of the present invention.

In accordance with this embodiment, a chamber 42 with a lateral series of two constriction portions 43 and 44 is prepared, and an organic solvent 45 containing lipid molecules is introduced into the chamber 42. By introducing three liquid droplets 46, 47, and 48 thereto, a first lipid bilayer 49 is formed on the contact surface of the liquid droplets 46 and 47, and a second lipid bilayer 50 is formed on the contact surface of the liquid droplets 47 and 48.

Figure 13:
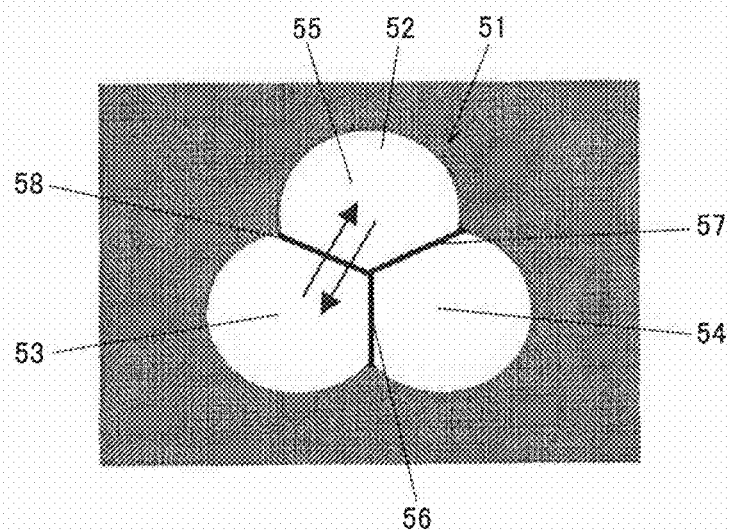
FIG. 13 is a schematic plan view of an apparatus for forming three lipid bilayers including a chamber with an outward appearance being substantially triangular shape in accordance with a fourth embodiment of the present invention.

FIG. 13 is a schematic plan view of an apparatus for forming three lipid bilayers including a chamber with the outward appearance being substantially triangular shape in accordance with a fourth embodiment of the present invention.

In accordance with the embodiment, a chamber 51 with outward appearance of substantially triangular shape is prepared. By introducing three liquid droplets 53, 54, and 55 into an organic solvent 52 containing lipid molecules, a first lipid bilayer 56, a second lipid bilayer 57, and a third lipid bilayer 58 can be formed on the contact surface of the liquid droplets 53 and 54, liquid droplets 54 and 55, and liquid droplets 55 and 53, respectively.

Figure 14:
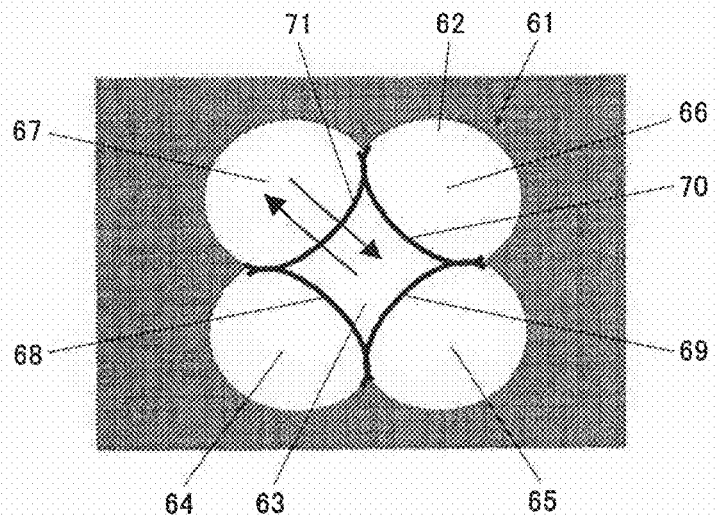
FIG. 14 is a schematic plan view of an apparatus for forming four lipid bilayers including the chamber with an outward appearance being substantially square shape in accordance with a fifth embodiment of the present invention.

FIG. 14 is a schematic plan view of an apparatus for forming four lipid bilayers including a chamber with the outward appearance being substantially square shape in accordance with a fifth embodiment of the present invention.

In accordance with the embodiment, a chamber 61 with outward appearance of substantially square shape is prepared, and five liquid droplets 63, 64, 65, 66, and 67 are introduced into an organic solvent 62 containing lipid molecules. In other words, a liquid drop 63 is placed in the center, and by setting liquid droplets 64, 65, 66, and 67 around it, a first lipid bilayer 68, the second lipid bilayer 69, the third lipid bilayer 70, and the fourth liquid bilayer 71 can be formed on the contact surface of the liquid droplets 63 and 64, liquid droplets 63 and 65, liquid droplets 63 and 66, and liquid droplets 63 and 67, respectively.

The shape of the chamber is not limited to those described above, but may have various modifications, as long as lipid monolayers may be formed on the interfaces of liquid droplets and the organic solvent containing lipid molecules, and a lipid bilayer may be formed at the constriction portion of a chamber, as described above.

Accordingly, a lipid bilayer can be formed by introducing liquid droplets, which is immiscible with an organic solvent, into the organic solvent containing lipid molecules beforehand, forming lipid monolayers, controlling the size of the liquid droplets, and contacting and fusing the lipid monolayers.

In the above described embodiments, the control of the liquid which is immiscible with the organic solvent containing lipid molecules is mainly described. However, it is also possible to carry out the control of the organic solvent containing lipid molecules. For example, it is possible to form a lipid bilayer by decreasing the pressure (or the volume) of the organic solvent containing lipid molecules, and thereby bringing into contact and fuse a plurality of monolayers.

In the above described embodiments, examples using an organic solvent containing lipid molecules are shown. However, it is also possible to use an organic solvent containing amphipathic molecules. As for amphipathic molecules, for example, phospholipids, long chain alcohols, long chain carboxylic acids, soaps, and synthetic detergents may be used, and these amphipathic molecules may form a monolayer on the interfaces of nonpolar solution/aqueous solution and vapor phase/aqueous solution.

The present invention is not limited within above embodiments, and various modifications are possible according to the object of the present invention, which should not be excluded from the scope of the present invention.

Following advantages may be achieved by the present invention.

(1) It is possible to perform a simple and an accurate bilayer formation.

(2) According to the invention as described in claims 2, 4, 7, and 8, the control of the pressure and volume of the liquid becomes possible by the control of syringe pumps, thereby the control of the film thickness becomes also possible, which dramatically improve reproducibility.

INDUSTRIAL APPLICABILITY

Membrane proteins play an important role in the physiological functions, such as drug responses, energy conversions, immune reactions, material transports and cellular signal transductions. In addition, most of the membrane proteins are the target for the drug discovery. For instance, the market size for drugs with respect to a series of membrane receptor protein called GPCR (G-protein coupled receptor) is large. Accordingly, the development of arrayed membrane proteins on a chip is hoped, but the effective reorganization of a planar lipid membrane on an array has not been reported. Moreover, a device for the simultaneous measurement of membrane current with the setting of physiological conditions has not been reported.

For instance, all the genes of GPCR are already identified by Human Genome Project, and the number of possible target is thus practically limited. It is therefore an urgent task to examine drug responses against each GPCR by arranging them on a chip in an array. Besides GPCR, a number of important targets for the drug design in the next generation include also membrane protein, such as a series of membrane proteins called ABC transporter which is considered to be the origin of the drug resistance of tumor cells. The development of the system based on the present invention may contribute to the quick development in drugs by incorporating the target membrane protein for drug discovery.

The invention claimed is:

1. An apparatus for forming a bilayer membrane by contact of amphipathic monolayers, the apparatus comprising:
   a) a substrate;
   b) a first microchannel formed on the substrate, wherein the first microchannel is supplied with an organic solvent comprising amphipathic molecules;
   c) a second microchannel formed on the substrate, orthogonally intersecting the first microchannel to form two opposing inlets;
   d) a square-shaped chamber at the intersection of the first and second microchannels, wherein a width of the square-shaped chamber is greater than widths of the two opposing inlets;
   e) at least one pump connected to ends of the second microchannel, said pump configured to supply the second microchannel with a liquid which is immiscible with the organic solvent; and f) a control unit connected to the at least one pump and configured such that a distance between opposing monolayer interfaces, which form between the organic solvent and the immiscible liquid in the square-shaped chamber, is controlled by pressure from the at least one pump allowing bilayer membrane formation by bringing the opposing monolayer interfaces into contact.

2. An apparatus for forming a bilayer membrane by contact of amphipathic monolayers, the apparatus comprising:

a) a substrate;

b) a chamber formed on the substrate, wherein the chamber comprises a plurality of compartments separated by at least one constriction portion, and the chamber is supplied with an organic solvent comprising amphipathic molecules; and c) a liquid unit configured for introducing at least one liquid immiscible with the organic solvent to the approximate center of each compartment to generate a liquid droplet therein, such that a distance between opposing monolayer interfaces, which form between the organic solvent and the immiscible liquid in the constriction portion, is controlled by the introducing of the immiscible liquid to enlarge the size of the liquid droplet allowing bilayer membrane formation by bringing the opposing monolayer interfaces into contact, wherein the compartments each consist of:

a floor situated in a lower plane of the substrate;

a curved wall optionally containing a first channel for introducing the organic solvent into the compartment, said wall partially surrounding and thereby enclosing the compartment such that an opening not surrounded by the wall faces an adjacent constriction portion; and optionally a ceiling situated in an upper plane of the substrate, said ceiling containing a second channel for the introducing of the immiscible liquid to the approximate center of the compartment.

3. The apparatus of claim 2, further comprising:

a) at least one first channel for introducing the organic solvent into the chamber;

b) the ceiling and at least one second channel for introducing liquid droplets into the approximate center of each compartment; and c) a control unit;

wherein the liquid unit comprises at least one pump connected to the second channel, and the control unit is connected to the at least one pump, which controls the sizes of the liquid droplets.

4. The apparatus of claim 1 or 3, wherein the pump is a syringe pump.

5. The apparatus of claim 1, 2 or 3, wherein the immiscible liquid is an aqueous solution.

6. The apparatus of claim 2 or 3, wherein the plurality of compartments comprises two compartments.

7. The apparatus of claim 2 or 3, wherein the plurality of compartments comprises three compartments.

8. The apparatus of claim 2 or 3, wherein the plurality of compartments comprises five compartments and the substrate is, or is approximately, square in shape.

9. The apparatus of claim 2, wherein the liquid unit comprises a pipette.

10. The apparatus of claim 1, further comprising:

g) a first electrode in a first inlet channel and a second electrode in a second inlet channel; and h) a measuring apparatus connected to the first electrode and to the second electrode.

11. The apparatus of claim 10, wherein the first inlet channel and the second inlet channel are the two opposing inlets of the second microchannel.

12. The apparatus of claim 11, wherein the first electrode, the second electrode, or both, comprise a Ag/AgCl electrode.

13. The apparatus of claim 11, wherein the first electrode and the second electrode comprise a Ag/AgCl electrode.

14. The apparatus of claim 11, wherein the measuring apparatus measures electric current and voltage.

15. The apparatus of claim 11, wherein:

the first electrode, the second electrode, or both, comprise a Ag/AgCl electrode; and the measuring apparatus measures electric current and voltage.

16. The apparatus of claim 9, wherein the chamber is opened in an upward direction, such that the compartments do not contain the ceiling.

17. The apparatus of claim 2, wherein the plurality of compartments are round or elliptical in shape.

* * * * *